United States Patent [19]

Rubin

[11] Patent Number: 4,584,368
[45] Date of Patent: Apr. 22, 1986

[54] β-GLUCURONIDASE ACTIVITY AND/OR PH-DEPENDENT PHARMACEUTICALS AND THIER METHODS OF PRODUCTION

[75] Inventor: David Rubin, 5 Rav Zair, Jerusalem, Israel

[73] Assignees: Adolf W. Schwimmer, Savoyon; Irwin S. Schwartz, Tel-Aviv; David Rubin, Jerusalem, all of Israel

[21] Appl. No.: 951,269

[22] Filed: Oct. 13, 1978

[51] Int. Cl.$^4$ .................... C07H 15/00; C07H 15/20
[52] U.S. Cl. .................................. 536/4.1; 548/156; 549/298; 549/417
[58] Field of Search ................................. 536/4, 4.1; 260/345.7 R; 549/298, 417; 548/156

[56] References Cited

U.S. PATENT DOCUMENTS

| | | | |
|---|---|---|---|
| Re. 29,465 | 11/1977 | Johnson | 536/4.1 |
| 2,798,079 | 7/1957 | Linn | 260/345.7 |
| 2,985,664 | 5/1961 | Krebs et al. | 260/345.7 |
| 3,758,455 | 9/1973 | Arita | 536/4.1 |
| 3,880,995 | 4/1975 | Jones | 536/4.1 |
| 3,959,253 | 5/1976 | Jones | 536/4.1 |

FOREIGN PATENT DOCUMENTS 2212014  10/1972  Fed. Rep. of Germany.

OTHER PUBLICATIONS

Bollenback, G. N. et al., "Jour. Amer. Chem. Soc.", vol. 77, pp. 3310-3315, 1955.
Wang et al., "Jour. Biol. Chem.", vol. 247, #9, pp. 2650-2651, 1972.
Chemical Abstracts, vol. 79, (1973), p. 533, Abstract No. 79138p, Matsunaga, Isao, "5-Chloro-7-iodo-8-quinolyl β-D-glucuronide".
Von Ardenne, M. et al, "Anti-Cancer Agents with Activation in Strongly Hyperacidified Tumor Tissue: CMT-Selectines," Agressologie, 1976, 17, 5,261-264.
Von Ardenne, M. et al, "Tumor pH and pH-Dependent Increases in the Toxicity of Anti-Neoplastic Drugs", Pharmazie 32 (2):74-75, 1977.
(D) Bicker, U., "Application of β-D-Glucuronides and Glucose Together Suggests a New Direction for Cancer Chemotherapy, Nature, 252, Dec. 20-27, 1974, pp. 726-727.
Sweeney, M. J., et al, "Possible In Situ Activation of Mycophenolic Acid by β-Glucuronidase", Cancer Research, 31, 477-478, Apr. 1971.
Kaneko, M., et al, "Synthesis of D-Glucuronic Acid Derivatives of 5-Fluorouracil Having O-Glycosidic Linkage," Chemical Phar. Bull., 25 (9), 2458-2460 (1977).
Baba, T., et al, "5-Fluorouracil-O-β-D-Glucuronide as a Newly Synthesized Chemically Modified, Non-Toxic Anticancer Drug", Gann, 69, 283,284, Apr. 1978.
Connors, T. A., "Cure of Mice Bearing Advanced Plasma Cell Tumors With Aniline Mustard: The Relationship Between Glucuronidase Activity and Tumor Sensitivity", Nature, Lond., 210, 866-867, 1966.
Bukhari, M. A., et al, "Aryl-2-Halogenoalkylamines XXVI-Glucuronic, Sulfuric and Phosphoric Esters of p-di-2-chloroethylaminophenol", Biochem. Pharm., 21, 963-967 (1972).
Ball, C. R., et al, "Enzyme-Activated Anti-Tumor Agents-Conjugates of p-hydroxyaniline Mustard as Substrates for Hydrolytic Enzymes", Biochem. Pharm., 23, 3171-3177, (1974).
Watabe, T. et al, "The Effect of Various Substituents on the Hydrolysis of Mono-substituted Phenol-β-D-Glucuronic Acids by β-Glucuronidase", Chem. Pharm. Bull. 18 (2) 414-415 (1970).
Fenselau, C. "Mandelonitrile β-Glucuronide: Synthesis and Characterization", Science, 198 (4317) 625-627, 1977.
Anghileri, L. J. et al, "β-Glucuronide Activity in Tumors: Accumulation of Radioiodinated Phenolphthalein", Oncology 25:19-32 (1971).
Mitchell, J. S. "Attempts to Develop Radioactive Drugs in the Treatment of Cancer", Radiotracer Tech. Appl. vol. 2, 1977, 1081-1110.
Gullino, P. M, et al, "Modifications of the Acid-Base Status of the Internal Milieu of Tumors", Journal of the National Cancer Institute, 34, 6, 857-869 (1965).
Levij, I. S., et al. "Inhibition by 2,4-Dinitrophenol of 9,10-Dimethyl-1,2-Benzanthracene Carcinogenesis in the Hamster Cheek Pouch", Oncology, 31, 334-337 (1975).
Merck Index, 9th Edition, 7325 "Podophyllotoxin", 1976.
Von Ardenne, M. et al, "Versuche zur Spaltung von β-D-Glukuroniden mit Kanzertoxisch Wirksamen Aglykonen Durch β-Glukuronidase bei pH 6," Zbl. Pharm. 116, vol. 6, pp. 563-572, (1977).

Primary Examiner—Johnnie R. Brown
Attorney, Agent, or Firm—Browdy and Neimark

[57] ABSTRACT

Hyperacidified tumors having high β-glucuronidase activity can be treated with glucuronides with aglycones toxic to the tumor cells with great safety toward the rest of the body by first administering an alkalinizing agent in an amount sufficient to maintain the pH level of non-tumor tissues at approximately 7.4 during the glucuronide treatment. This will cause inactivation of β-glucuronidase activity in the rest of the body. Novel glucuronides are disclosed the aglycones of which exert a higher toxic effect in an acid environment or is water-soluble only in an alkaline environment. Such compounds have particular utility with the above process. By substituting radioisotopes into the aglycone, diagnosis and in situ radiation therapy may be accomplished. Bacterial cells having β-glucuronidase activity may also be diagnosed and treated in accordance with the present invention. A urine test is disclosed to determine the amount of free glucuronic acid in the urine which is an indication of the presence of a tumor in the body having high β-glucuronidase activity.

2 Claims, No Drawings

β-GLUCURONIDASE ACTIVITY AND/OR PH-DEPENDENT PHARMACEUTICALS AND THIER METHODS OF PRODUCTION

FIELD OF THE INVENTION

The present invention relates to the treatment of certain bacterial infections having β-glucuronidase activity. The present invention further relates to a new class of glucuronides whose aglycone's activity or water solubility is pH dependent as well as the method of preparation of such glucuronides.

BACKGROUND OF THE INVENTION

There have been many reports in the prior art relating to the general concept of providing direct transport of an agent which is toxic to tumor cells directly to tumors having β-glucuronidase activity by conjugating the agent with glucuronic acid. Among such reports are Von Ardenne, M. et al. *Agressologie*, 1976, 17, 5, 261-264; East German Pat. No. 122,386; German Offenlegungsschrift No. 22 12 014; Sweeney et al, *Cancer Research*, 31, 477-478, April 1971; Baba et al, *Gann*, 69, 283-284, 1978; and Ball, C. R., *Biochem. Pharm.*, 23, 3171-3177 (1974).

The Von Ardenne reference suggests broadly many types of aglycones which may be conjugated to glucuronic acid and will be active at the tumor site. These include, broadly, alkylating groups, antimetabolites, cytotoxins, membrane-active (lytic) groups, glycolysis stimulators, respiration inhibitors, inorganic and organic acids and cell cycle stoppers. The East German patent also suggests many such combinations including 5-fluorouracil-glucuronide, methotrexate-glucuronide, 6-mercaptopurene-glucuronide, aniline mustard-glucuronide and many others. The Offenlegungsschrift also mentions a large number of glucuronides. The Sweeney article relates to the anti-tumor activity of mycophenolic acid-β-D-glucuronides, Baba relates to the anti-tumor activity of 5-fluorouracil-O-β-D-glucuronide, and Ball relates to the anti-tumor activity of p-hydroxyaniline mustard glucuronide.

It has also been reported that the selectivity of this transport mechanism can be improved by hyperacidification of the tumor cells. The Von Ardenne reference supra, as well as the East German patent, clearly recognize the importance and the feasibility of hyperacidification of the tumor cells when using the glucuronide mechanism. The Von Ardenne reference speaks of a method that yields a pH difference of at least 1 pH unit and may therefore be used as a basis for selectivity. It refers to reaching steady state conditions after hyperacidification in which the brain pH is 7.0 and the tumor tissue pH is approximately 5.5 to 6.0. Note also Von Ardenne, M. et al, *Pharmazie*, 32 (2): 74-75, 1977.

Bicker, U., *Nature*, 252, Dec. 20-27, 1974, pp. 726-727, particularly notes that lysosomal enzyme β-glucuronidase has an optimum pH of 5.2 and that for anti-tumor activity of glucuronides, the pH must be lowered such as by the administration of glucose. Experiments are detailed which indicate that the hyperacidification by glucose is necessary in order to obtain significant deconjugation of the glucuronides.

Even with hyperacidification of the tumor cells by known methods as, for example, glucose administration, however, there is still a problem in that other organs and tissues of the body which have a naturally occurring high β-glucuronidase activity, will also release the toxic aglycones and thereby cause damage to healthy tissues. This is most particularly a problem with regard to the kidney which normally has an acid pH environment.

Another problem faced by the prior art is the fact that it is very difficult to synthesize glucuronides when the aglycone is a strong electron acceptor. This is because the glucuronide will become deconjugated (hydrolyzed) in the course of the classical process. U.S. Pat. No. 2,985,664 discloses a process for preparing a glucuronide in which the aglycone is a strong electron acceptor. However, the process suggested by this patent is not reproducable. Fenselau, C., *Science*, 198 (4317) 625-627, 1977, relates to a biosynthesis process for producing a glucuronide in which the aglycone is a strong electron acceptor. However, the problem still remains how to produce such a compound by chemical synthesis in a reproducible manner.

SUMMARY OF THE INVENTION

Accordingly, it is an object of the present invention to overcome the deficiencies of the prior art.

It is an object of the present invention to provide new compounds and pharmaceutical compositions which have very low toxicity to the organism as a whole but very high selective toxicity toward tumor cells, and particularly tumor cells having high β-glucuronidase activity.

It is another object of the present invention to provide a process of preparing the compounds which may be used in such a process.

It is still another object of the present invention to provide a process for the treatment of bacterial infections when the bacteria exhibit β-glucuronidase activity.

These and other objects of the present invention will be better understood from a reading of the following summary and the detailed description of the present invention.

It has now been found that the selectivity of glucuronide compounds toward tumors can be greatly increased and the possible deconjugation of the toxic aglycones in normal parts of the body can be greatly minimized by administering to the patient, prior to or simultaneously with administration of the glucuronide, an alkalinizing agent which will maintain the pH of the test of the body at a pH of about 7.4. It is known that at a pH of 7.4 and above β-glucuronidase activity is substantially nil. Thus, the administration of alkalinizing agents such as bicarbonates or other basic salts will substantially decrease and eliminate β-glucuronidase activity which naturally occurs in certain healthy tissues such as the kidneys, spleen, and liver. Such an administration of alkalinizing agent will not diminish the acidity of the tumor cells themselves, however, in view of the naturally low pH of the tumor cells, the mechanism of prior hyperacidification, and the lack of substantial blood perfusion through the tumor areas, as well as other possible mechanisms. It has been suggested in the literature, in fact, that bicarbonate will actually increase the acidity of the cancer cells. Gullino, P. M., et al, *J.N.C.I.*, 34, 6, 857-869 (1965).

Since the β-glucuronidase activity of the tumor cells will be enhanced by acidification, and the β-glucuronidase activity of the rest of the body, particularly of the kidneys, will be substantially eliminated by alkalinization, the toxic aglycones will only be released at the tumor site itself due to deconjugation of the glucuronides by the action of β-glucuronidase. Without the alkalinization step, substantial amounts of toxic materials may be released, for example, in the kidneys, and the toxic aglycones so released may cause substantial damage to these organs. Thus, only through the use of the present invention can glucuronides of compounds toxic to tumor cells be used clinically with a great degree of safety. The greater the toxicity of the aglycones, the more important is the alkalinization step.

A further feature of the present invention is the use of certain novel glucuronide compounds which are particularly suitable for use in the present invention because of the significant pH differential between the tumor cells and surrounding healthy tissue. If the aglycone is more active at lower pH, or non-polar in acid condition and becoming polar only in alkaline condition, i.e. the aglycone is water-soluble at pH ranges above about 7 and lipid-soluble at pH ranges below 7, then the selectivity of the present invention is further increased. Using these new compounds, even if there is deconjugation elsewhere in the body, the aglycone will be water-soluble due to the alkaline pH and be washed out of the system quickly. However, in the low pH range of the hyperacidified tumor cells, the aglycone will actually become attached to the tumor cells and will not become solubilized and washed away. Even if some amount of aglycone becomes removed from the locus of the tumor cells, they will immediately come into an alkaline environment and thus become water soluble and be quickly swept from the body.

Among the novel glucuronides in this category are 2,4-dinitrophenol β-D-glucuronic acid; chloro-m-cresol β-D-glucuronic acid; 4,6-dinitro-o-cresol β-D-glucuronic acid; 4-chloro-3,5-xylanol β-D-glucuronic acid; chlorothymol β-D-glucuronic acid; 2-phenyl-6-chlorophenol β-D-glucuronic acid; 5-chloro-7-iodo-8-quinolinol β-D-glucuronic acid; and podophyllotoxin β-D-glucuronic acid. The chloro-m-cresol β-D-glucuronic acid is of particular interest as it actually loses its toxic activity in an alkaline environment.

Aside from the anti-tumor utility, these novel compounds, and any other glucuronide compounds having cytotoxic aglycones, also have an anti-bacterial activity, particularly against those types of bacteria having β-glucuronidase activity. It is known, for example, that streptococcus, staphylococcus and *E. coli* bacteria have β-glucuronidase activity. Therefore, if the glucuronides come into contact with these bacteria, they will become deconjugated and the cytotoxic aglycones will be toxic to the bacteria.

It has been reported that the optimum pH of bacterial β-glucuronidase is higher than the optimum pH of the β-glucuronidase of normal healthy internal organs, such as liver, spleen, kidney, etc. Therefore, upon alkalinization of the body in accordance with the method discussed hereinabove, the β-glucuronidase activity of the organs will be substantially eliminated, while that of the bacteria, although alkalinized, will still be present. The administered glucuronide will then only be deconjugated to its active form at the site of the infection. Since tumor cells are not being treated for this utility, no hyperacidification step is necessary.

While the glucuronide compounds discussed hereinabove are preferred for use in the process of the present invention, it should be understood that the glucuronides of any anti-tumor drug, including those previously suggested in the prior art as being useful, may be used to greater advantage in the process of the present invention since the selectivity thereof will be increased by the alkalinization step. Non-limiting examples of compounds, some of which may have been known, which may also be used in the present invention, even though they have no presently known differentiation of toxicity or solubility which is pH dependent, include 5-fluorouracil-O-β-D-glucuronic acid; p-hydroxyaniline mustard β-D-glucuronic acid; methotrexate β-D-glucuronic acid; floxuridine β-D-glucuronic acid, cytarabine β-D-glucuronic acid; melphalan β-D-glucuronic acid; hydroxyurea β-D-glucuronic acid; adriamycin β-D-glucuronic acid; thiouracil β-D-glucuronic acid, etc.

Another feature of the present invention relates to the process of preparing the glucuronides. It has been discovered that it is impossible to prepare conjugates of glucuronic acid by the classical methods when the aglycone is a strong electron acceptor, as these compounds must first be prepared as the methyl ester of the glucuronic acid and it is not possible by the classical methods to convert the methyl ester to the acid without deconjugating the aglycone. While barium methoxide has been suggested for this purpose in a related process in U.S. Pat. No. 2,985,664, it has been discovered that barium methoxide will not work. However, it has now been discovered that if barium hydroxide is used, the methyl ester of the aglycone of the glucuronide may be converted to the barium salt, and the barium salt may be converted to the free acid by the use of sulfuric acid without deconjugation of the glucuronide. Moreover, removal of the acetyl protecting groups is accomplished in the same step, thus eliminating the need of a separate step to accomplish this function.

Because of the acid-alkaline differentiation between the tumor cells and the rest of the body achievable by the process of the present invention, it is possible to use certain compounds which denature cytoplasmic proteins or affect the energy supply of the cells directly without first conjugating with the glucuronic acid. This can only be done, however, if the compound is one whose activity or solubility is pH-dependent. Examples of such compounds are 2,4-dinitro-phenol; chloro-m-cresol; 4,6-dinitro-o-cresol; 4-chloro-3,5-xylanol; chlorothymol; 2-phenyl-6-chlorophenyl; 5-chloro-7-iodo-8-quinolinol; and podophyllotoxin. The use of these compounds directly without first conjugating with glucuronic acid would be particularly useful in treating tumors with no demonstrated β-glucuronidase activity.

Another feature of the present invention is related to the extremely high tumor selectivity which is achievable in accordance with the present invention. In view of the selectivity, if one or more of the atoms of the aglycone is exchanged with a radioactive isotope, a local radioactivity can be exerted. This method is not only important for diagnostic purposes to trace the tumor and its metastases, but if an isotope is chosen with β-radiation activity, then this method may also be used for local radiation treatment at the cancer site. This use of radioactive isotopes is particularly important when using an aglycone which is known to be non-polar in acid condition and polar in alkaline condition. When this quality exists, the aglycone is accumulated at the cancer site not only because of the β-glucuronidase activity, but also because of its insolubility in water at the cancer site. At the same time, the compounds with the radioactive isotopes are washed away from the rest of the body. The use of p-iodophenol β-D-glucuronic acid produces an aglycone, p-iodophenol, which fulfils these demands. A radioactive isotope of iodine can be used as the iodine constituent of this compound. It is preferable to use $^{131}I$ for labelling and $^{133}I$ for treatment, as the former is richer in gamma radiation while the latter is richer in beta radiation. In order to prevent the iodine from migrating to the thyroid gland, premedication with non-radioactive Lugol's solution may be used for saturation the thyroid gland.

Another compound which can be easily radioactive labelled is the glucuronide of phenylsulfazole. A radioactive sulfur atom can be used. This compound does not migrate to the thyroid gland, and the aglycone is not soluble in water.

Before treatment of patients in accordance with the present invention, it should be ascertained that the particular type of tumor involved has high $\beta$-glucuronidase activity. This may be done in a number of ways. One way is to assay tumor cells obtained in a biopsy for $\beta$-glucuronidase activity. If such a test is positive, then the pharmaceutical compositions of the present invention may be administered.

A second method is the administration of a glucuronide whose aglycone has been labelled with a radioactive isotope. If upon a full body scan it is found that the radioisotope is accumulated at any specific areas of the body, then this will indicate not only the location of the tumor but the fact that the tumor has sufficient $\beta$-glucuronidase activity to deconjugate the glucuronide. After this has been determined, the appropriate amount of the glucuronide of choice may be administered. If there are no tumors present, or if the tumors are of the type which do not have $\beta$-glucuronidase activity, then there will be no accumulation of radioisotope in the body as the alkalinization step of the present invention eliminates all usual $\beta$-glucuronidase activity and the isotope will be passed through the body.

Another method of diagnosing tumors which are treatable by means of the present invention is to test for the presence of free glucuronic acid in the urine. While the presence of glucuronides in the urine is common, the presence of free glucuronic acid is not usual. Thus, the presence of free glucuronic acid in the urine, and particularly the presence of increasing amounts of glucuronic acid when tested over a period of several days, is a potent indication of the presence of tumors with $\beta$-glucuronidase activity. It is hypothesized that the presence of free glucuronic acid in the urine in the cancer patients is caused by the action of $\beta$-glucuronidase in the cancer cells on the intercellular filaments and connective tissue. Glucuronic acid is a reaction product of such activity because the intercellular filaments and connective tissue are composed of polymers of which glucuronic acid is an element and which are known substrates for the enzyme $\beta$-glucuronidase.

A method of distinguishing free glucuronic acid from conjugated glucuronides in the urine is another feature of the present invention. Both glucuronides and glucuronic acid give a chromogenic complex with tetraborate in concentrated sulfuric acid which reacts with m-hydroxydiphenyl to create a colored water-soluble complex. When lead acetate is added at an alkaline pH, the glucuronides precipitate and the addition of ditizone (dithiosemicarbizone) makes a stable complex with the excess lead. Accordingly, an optical reading may be taken representative of the amounts of total glucuronides and free glucuronic acid after tetraborate and m-hydroxydiphenyl have been added. A second reading may then be taken after the conjugated glucuronides and excess lead have been removed from the aqueous phase by the addition of basic lead acetate and after ditizone has been added.

DESCRIPTION OF THE PREFERRED EMBODIMENTS

While many glucuronide compounds having aglycones which are toxic to cancer cells have been described theoretically in the literature, very few have actually been produced. This is because they are very difficult to synthesize, particularly when the aglycone is a strong electron acceptor. The improved method of the present invention avoids the problem and permits the production of conjugates of glucuronic acid of almost any type of aglycone. The standard methods can be used to form the methyl ester of the triacetyl glucuronic acid conjugates, but it is often quite difficult to go from the triacetyl methyl ester to the glucuronic acid conjugate. This problem has been solved by treatment in accordance with the process of the present invention.

The glucuronides in accordance with the present invention and for use in the process of the present invention, may be synthesized from methyl(tri-O-acetyl-$\alpha$-D-glucopyranosyl bromide)-uronate which is the active glucuronic acid and is formed in accordance with the teachings of Bollenback, G. N., et al, *J. Am. Chem. Soc.* 77, 3310, (1955). This compound is condensed with the aglycone in a solution of quinoline, phenol, methyl cyanide or methyl nitrite catalyzed by silver oxide or silver carbonate. Another method of condensation is to use sodium or potassium hydroxide as the condensing agent in aqueous acetone solution. The reaction scheme is illustrated as follows:

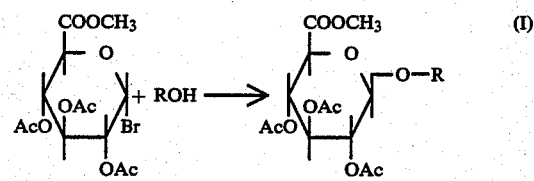

wherein ROH is the desired aglycone.

If the methyl ester of the glucuronide is desired, the protecting acetic acid groups may be removed by anhydrous sodium methoxide or anhydrous barium methoxide in accordance with the following reaction:

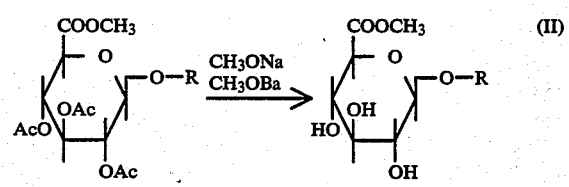

The acid may be produced by reacting the triacetyl methyl ester with barium hydroxide to produce the barium salt in accordance with the following reaction:

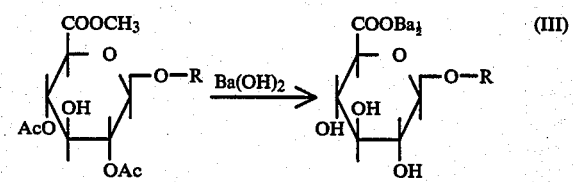

This barium salt of the glucuronide precipitates. An equimolar solution of sulfuric acid releases the free glucuronide according to the following reaction:

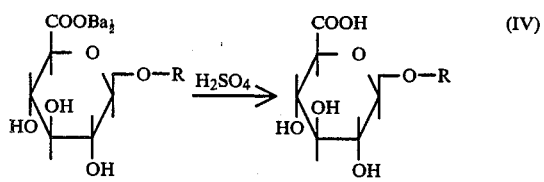
(IV)

Example I shows the preparation of 2,4-dinitrophenol-$\beta$-D-glucuronic acid.

EXAMPLE I

Synthesis of 2,4-Dinitrophenol-$\beta$-D-glucuronic Acid

Methyl-(2,3,4-tri-O-acetyl-$\alpha$-D-glucopyranosyl bromide)-uronate was prepared in accordance with the process of Bollenback, G. N., et al, *J. Am. Chem. Soc.* 77, 3310 (1955). Four grams of methyl(tri-O-acetyl-$\alpha$-D-glucopyranosyl bromide)-uronate in acetone (80 ml) and 8.9 g 2,4-dinitrophenol were treated with 5N potassium hydroxide (9 ml) and the solution kept at 25° C. for 24 hours, then diluted with 3 volumes chloroform. The chloroform-acetone layer was washed with water and dried. Removal of the solvent and two recrystallizations from acetone yielded the methyl-2,3,4-tri-O-acetyl-$\beta$-D-glucopyranosyl uronate of 2,4-dinitrophenol.

The free acid form of the compound was formed by treating the 2,4-dinitrophenyl-methyl(tri-O-acetyl-$\beta$-D-glucopyranosyl bromide)-uronate with a one-half molar amount of barium hydroxide to produce the barium salt. This barium salt of the glucuronide precipitates as a white amorphous material. An equimolar solution of $H_2SO_4$ releases the free glucuronide. Distillation of the supernatant yielded bright yellow-brown crystals having a melting point of 179°–180° C. This compound was incubated with $\beta$-glucuronidase and produced 2,4-dinitrophenol, thus confirming that the final product is indeed 2,4-dinitrophenol-$\beta$-D-glucuronic acid.

Each of the other glucuronides in accordance with the present invention, e.g. chloro-m-cresol-$\beta$-D-glucuronic acid; 4,6-dinitro-o-cresol-$\beta$-D-glucuronic acid; 4-chloro-3,5,-xylanol-$\beta$-D-glucuronic acid; chloro-thymol-$\beta$-D-glucuronic acid; 2-phenyl-6-chlorophenol-$\beta$-D-glucuronic acid; 5-chloro-7-iodo-8-quinolinol-$\beta$-D-glucuronic acid; and podophyllotoxin-$\beta$-D-glucuronic acid, as well as p-iodophenol-$\beta$-D-glucuronic acid and phenylsulfazole-$\beta$-D-glucuronic acid, may be made in a similar manner by reacting a stoichiometric excess of the aglycone with the methyl-(tri-O-acetyl-$\beta$-D-glucopyranosyl bromide)-uronate in 5 normal potassium hydroxide and maintaining the reaction solution at room temperature for 24 hours. The solution is then diluted with 3 volumes chloroform and the chloroform-acetone layer washed with water and dried. After removal of the solvent, the crystals which are obtained are treated with a one half molar amount of barium hydroxide to produce the barium salt which is then treated with an equimolar solution of sulfuric acid to produce the free glucuronide.

The free acid form of the glucuronide, or a salt thereof which will ionize at the conditions of use, is the preferred form of the compounds to be used in accordance with the present invention. However, pharmaceutically acceptable esters may also be used, although in most cases it would be expected that their activity would be somewhat lower due to their relatively lower affinity to $\beta$-glucuronidase. This is particularly true with respect to aglycones which are strong electron acceptors. Accordingly, whenever the term "glucuronide compound" is used in the present specification and claims it is understood to include not only the free glucuronic acid form of the conjugate but also pharmaceutically acceptable salts and esters thereof as discussed hereinabove.

Prior to therapeutic treatment with compounds of the present invention, the presence of tumor having high $\beta$-glucuronidase activity must be diagnosed. The most positive way to definitively ascertain whether a tumor is present having high $\beta$-glucuronidase activity is to conduct a biopsy and to assay the tumor cells obtained for $\beta$-glucuronidase activity. This, of course, is not feasible for most kinds of tumor. Another way to diagnose for the presence of tumors having $\beta$-glucuronidase activity, is to conduct a urine test in order to determine the presence of free glucuronic acid. Normal patients show between 200 to 400 mg per 24 hours of free glucuronic acid in the urine. Cancer patients with well developed tumors which have $\beta$-glucuronidase activity will show greater than 2,000 to 7,000 mg per 24 hours free glucuronic acid. Accordingly, using the test of the present invention, if substantially more than 400 mg per 24 hours of free glucuronic acid is shown, then this is an excellent indication of the presence of tumors having high $\beta$-glucuronidase activity.

A negative indication on this urine test will not conclusively rule out the presence of tumors having $\beta$-glucuronidase activity, because tumors in their initial stages, though they might have $\beta$-glucuronidase activity, might not release sufficient free glucuronic acid to cause a positive reading of the urine. Therefore, the urine test should be repeated, and if an increasing amount of free glucuronic acid is found, then this is another indication of the presence of a tumor having $\beta$-glucuronidase activity. An example of the method of determining the amount of free glucuronic acid in the urine is given in Example II.

EXAMPLE II

Test for Glucuronic Acid in Urine

Both glucuronides and glucuronic acid give a chromogenic complex with tetraborate and concentrated sulfuric acid which reacts with m-hydroxydiphenyl to create a colored water-soluble complex. Furthermore, glucuronides precipitate with basic lead acetate when pH is 8, while the free glucuronic acid is not affected by the lead acetate. Complexing the excess lead with dithiocarbizone forms a stable complex with lead which can be removed, thus leaving free glucuronic acid.

To 10 cc of a urine sample 0.1N ammonium hydroxide is added until a pH of 8 is reached. An excess of saturated solution of basic lead acetate is then added causing precipitation of the conjugated glucuronides. The sample is then centrifuged and the supernatent separated. Two cc of the supernatant is then treated with 10 cc of 10% dithiocarbizone (ditizone) in chloroform in order to remove the excess lead. After waiting until the separation is complete, the aqueous phase is separated. To 0.2 cc of the aqueous phase is added 1.2 cc of sodium tetraborate in concentrated $H_2SO_4$. The mixture is mixed well in a test tube and chilled in crushed ice. The test tube is then heated for 5 minutes in boiling water and immediately cooled in ice until it becomes cold. Twenty microliters of 0.15% m-hydroxydiphenyl in 0.5% NaOH is then added. After waiting 5 minutes, the optical density is read at a wavelength of 5200 Å. The reading obtained represents the amount of free glucuronic acid present in the urine.

The total amount of free and conjugated glucuronic acid is simply determined by directly treating the sample with tetraborate and hydroxydiphenyl, without first removing the free glucuronides. Reading at a wavelength of 5200 Å will give the indication of the total amount of conjugated glucuronides and free glucuronic acid which is present.

EXAMPLE III

Method of Administration of Glucuronide Therapy

After it has been determined that the patient has a tumor with β-glucuronidase activity, the first step of the treatment is to give him a dose of glucose as, for example, 100 g of honey, glucose or other sugar. Approximately 1 hour later, an intravenous drip is begun of a solution in distilled water containing approximately 10% glucose and 60 milliequivalents sodium bicarbonate. Approximately 1 liter is administered, assuming no contraindications, and the pH of the urine is checked to determine that it has reached a pH of approximately 7.4. This will establish that the system has become alkalinized and it is now safe to administer the glucuronide. Another liter of the same glucose-bicarbonate solution, but also including the desired amount of glucuronide, is then administered. This is repeated daily as needed.

If there are contraindications for the administration of bicarbonate, then antacid may be orally administered. The important criterion is that the pH of the urine become approximately 7.4 and remain so during treatment.

The hyperacidification of the tumor cells is caused by a hyperglycemic condition in the patient. Therefore any hyperglycemic agent may be used as the hyperacidification agent, as for example, fructose, galactose, lactose or glucagon. Furthermore, it should be understood that this hyperglycemic condition may be effected in any known manner. For example, if the patient is diabetic then the condition can be brought about by decreasing the insulin administration.

Any agent which will raise the pH of the urine to approximately 7.4 can be used as the alkalinizing agent, including sodium or potassium bicarbonate or citrate, or other basic salts or antacids. While it is preferred that these be administered intravenously, they may be administered orally.

When the term "approximately 7.4" is used in the present specification and claims, with respect to the pH level to be maintained in the rest of the body, it should be understood that a pH level slightly above or below 7.4 may be used, although not preferred. As the pH decreases from 7.4 the β-glucuronidase activity increases (until the optimal pH is reached). Furthermore, below pH 7.0 the rest of the body will not be alkaline but will be acid. Above 7.4 the danger of alkalosis increases without any substantial further decrease in β-glucuronidase activity. A pH level of 7.4 is preferred as this is physiological pH and cannot be harmful to the body and it is known that the β-glucuronidase activity in healthy organs is substantially nil at this pH level.

The dosage of the glucuronides should be monitored to avoid any side effects due to the massive release of toxins caused by the dying cancer cells. It may be preferble to treat with glucuronides in short courses of several days, leaving several days in between, to allow any toxins released by the dying cancer cells to leave the body before the further treatment continues.

Besides intravenous administration, the glucuronides may be administered by any means of parenteral administration. However, the glucuronides should not be administered orally as it is known that β-glucuronidase is present in the digestive tract.

The amount of glucuronide to be administered to any given patient must be determined empirically and will differ depending on the condition of the patient. Relatively small amounts of glucuronide can be administered at first with steadily increasing daily dosages if no adverse effects are noted. Of course, the maximum safe toxicity dosage as determined in routine animal toxicity tests should never be exceeded.

It is clear that any tumor cells having β-glucuronidase activity may be treatable in accordance with the present invention with the remaining organs of the body being protected by the alkalinization step. Tumors which are known to have β-glucuronidase activity include solid breast tumors and their metastases, tumors of the large intestine and their metastases, bronchogenic carcinoma and its metastases, and lymphomas. It is also known that neoplasms that do not have high β-glucuronidase activity, and therefore cannot be treated in accordance with the present invention, include leukemia. It must be understood, however, that this list is not meant to be complete, and that the prior art is aware of many other tumors that have β-glucuronidase activity. However, whether or not the art is presently aware that any given tumor has β-glucuronidase activity, this can be determined by any of the various methods of diagnosis discussed in the present application and if it is determined that the tumor does have β-glucuronidase activity, the therapeutic treatment of the present invention can be effectively used.

EXAMPLE IV

Method of Administration of Radioisotopes

If an aglycone labelled with a radioactive isotope is to be administered, the labelling may be accomplished by any method known per se. For diagnostic purposes only, relatively small amounts of these labelled glucuronides may be administered. They are otherwise administered in the same manner as set forth in Example III for non-labelled glucuronides. Scanning of the body to determine whether any of the radio-labelled aglycone is retained by the body will indicate whether a tumor is present having β-glucuronidase activity and will also indicate where the tumor or any metastases thereof may be found. As noted above, gamma ray emitting isotopes, such as $^{131}$I, are particularly suitable for this purpose.

The radio-labelled glucuronides may also be used for in situ radiation therapy, particularly if an isotope is used having high beta-radiation activity, such as $^{133}$I. This will give the dual effect of attacking the cancer cells not only with the toxic aglycones but also with the beta-radiation. Again, the method of administration will be the same as set forth in Example III.

Another utility for the present invention is the use of the boron-containing aglycone. It is already known that if boron atoms are bombarded with neutrons, they will break into lithium with the consequent release of positrons. If the boron atoms are attached to tumor tissue at the time, the positrons will be abruptly absorbed by the tumor tissue which will be lethal thereto. This process will have outstanding utility when the boron atoms are concentrated exclusively at the tumor cells in accordance with the process of the present invention.

EXAMPLE V

Method of Administration of pH Dependent Therapy

If the tumor cells are hyperacidified and the healthy tissue alkalinized in accordance with the method set forth in Example III, an acid-alkaline pH differential will be created between the tumor cells and healthy cells. Thus, compounds whose activity or solubility is pH-dependent may be administered directly, without first conjugating with a glucuronide. Such compounds will selectively attack the acidified tumor cells without harming the remainder of the body which has an alkaline pH.

As in the method of Example III, the patient is first given an oral dose of hyperglycaemic agent, such as 100 g of honey, glucose or other sugar. Approximately 1 hour later, an intravenous drip is begun of a solution in distilled water containing approximately 10% glucose and 60 milliequivalents sodium bicarbonate. Approximately 1 liter is administered, assuming no contraindications, and the pH of the urine is checked to determine that it has reached a pH of approximately 7.4. This will establish that the system has become alkalinized and it is now safe to administer the acid-active compound. Another liter of the same glucose-bicarbonate solution, but also including the desired amount of acid-active compound, is then administered. This is repeated daily as needed.

Compounds such as 2,4-dinitrophenol; 4,6-dinitro-o-cresol; 4-chloro-3,5-xylanol; chlorothymol; 2-phenyl-6-chlorophenol; 5-chloro-7-iodo-8-quinolinol and podophyllotoxin are all water-soluble at alkaline pH's and lipid-soluble at acid pH's. Therefore, if the compounds are administered in the manner discussed above they will not create substantial harm to healthy tissue because they will be washed through the system relatively quickly. At the site of tumor tissue with acid pH, however, these compounds will come out of water solution and exert their cytotoxic or energy-supply effecting action on the tumor cells.

Compounds such as chloro-m-cresol, as well as 4,6-dinitro-o-cresol, 4-chloro-3,5-xylanol, chlorothymol and 2-phenyl-6-chlorophenyl are more active at lower pH. Therefore, administration of these compounds with concomitant hyperacidification of the tumor cells and alkalinization of the remainder of the body will be even less harmful to healthy tissue, as their activity is diminished at the pH of the healthy tissue.

The dosage of the non-glucuronide compounds in accordance with this embodiment of the present invention will generally be somewhat less than the corresponding glucuronides as the glucuronide form of the compounds is substantially less toxic than the free compounds. The precise dosage must be determined empirically depending on the condition of the patient. Relatively small doses should be administered at first with steadily increasing daily dosage if no adverse effects are noted. Of course, the maximum safe toxicity dosage as determined in routine animal toxicity tests should never be exceeded.

Alternative acidifying and alkalinizing agents, as discussed hereinabove with respect to the glucuronide embodiment, may also be used with the present embodiment.

EXAMPLE VI

Method of Anti-Bacterial Administration

Glucuronide administration may be used in the treatment of bacterial infections if the bacteria involved are known to have $\beta$-glucuronidase activity. Examples of such bacteria are streptococci, staphylococci, and *E. coli*. The method of treatment of such bacterial infections will be similar to the method set forth in Example III except that no hyperacidification will be necessary. This is so because bacterial $\beta$-glucuronidase is active at higher pH levels than $\beta$-glucuronidase of normal healthy internal organs. Furthermore, such a hyperacidification step would not affect the pH of the bacteria as its mechanism is specific to tumor cells.

The first step in antibacterial administration is an intravenous drip of distilled water and 60 milliequivalents sodium bicarbonate. Approximately one liter is administered and the pH of the urine is checked to determine that it has reached a pH of approximately 7.4. Another liter of the same bicarbonate solution, but also including the desired amount of glucuronide, is then administered in the same manner. This treatment may be repeated daily, if necessary.

The alkalinizing agent may also be orally administered and any agent may be used that will alkalinize the body to an extent such that the pH of the urine becomes approximately 7.4. The glucuronide should not be administered orally but it may be administered by any means of parenteral administration.

Certain known anti-bacterial drugs having adverse side-effects may also be administered as glucuronides in accordance with the method of the present invention in order to reduce or eliminate these adverse effects. For example, chloroamphenicol is known to have a bone marrow depression effect which will not take place if the glucuronide is used. Neomycin is a known antibacterial which cannot be administered internally because of its toxicity. However, it can be orally administered for the treatment of infections of bacteria having high $\beta$-glucuronidase activity if first conjugated to glucuronic acid.

The radioisotope-labelled aglycone diagnostic procedure discussed hereinabove with respect to tumor diagnosis may also be used to determine the existance and location of bacterial infections. For example, a patient complaining of pain in the area of the appendix can receive the radio-labelled glucuronides. If no accumulation of isotope is found in the area then inflammation caused by bacteria with $\beta$-glucuronidase activity as a cause of the pain can be ruled out. In most instances inflammation in appendicitis is due to infection by bacteria with $\beta$-glucuronidase activity. Other use of such a diagnostic procedure would be obvious to those skilled in this art.

Besides the glucuronide compounds discussed hereinabove, any known conjugatable antibiotic may be conjugated with glucuronic acid for use against $\beta$-glucuronidase containing infections. This has the advantage of greatly diminishing the amount of free antibiotic circulating in the blood stream. The only antibiotic which is released will be released at the site of the infection. Therefore much smaller dosages may be given. Accordingly, the glucuronides of the present invention can serve as an internally administered local antibiotic. Because of the known $\beta$-glucuronidase activity in the digestional tract no glucuronide should be administered orally, although any mode of parenteral administration is permissible.

If the antibiotic aglycone is known not to have any effect on the kidneys, then the alkalinization step can be eliminated. Many antibiotics, however, are known to be nephrotoxic to some extent and thus the alkalinization step is important to protect the kidneys.

It will be obvious to those skilled in the art that various changes may be made without departing from the scope of the invention and the invention is not to be considered limited to what is described in the specification.

What is claimed is:

1. A compound selected from the group consisting of 2,4-dinitrophenol $\beta$-D-glucuronic acid; chloro-m-cresol $\beta$-D-glucuronic acid; 4,6-dinitro-o-cresol $\beta$-D-glucuronic acid; 4-chloro-3,5-xylanol $\beta$-D-glucuronic acid; chlorothymol $\beta$-D-glucuronic acid; 2-phenyl-6-chlorophenol $\beta$-D-glucuronic acid; podophyllotoxin $\beta$-D-glucuronic acid; p-iodophenol $\beta$-D-glucuronic acid; and phenylsulfazole $\beta$-D-glucuronic acid.

2. A method for the production of conjugates of free glucuronic acid with aglycone which are strong electron acceptors, comprising:

condensing said aglycone with methyl(tri-O-acetyl-$\alpha$-D-glucopyranosyl)halide-uronate to form the methyl ester of the aglycone-tri-O-acetyl-$\beta$-D-glucuronic acid;

adding to the product of said condensing step a sufficient quantity of barium hydroxide to produce a precipitate;

separating said precipitate;

treating said precipitate with a sufficient quantity of sulfuric acid until precipitation of barium sulfate is completed;

removing the supernatant from the product of said treating step; and drying said supernatant to obtain the free glucuronic acid conjugate of said aglycone.

* * * * *